(12) United States Patent
Stein et al.

(10) Patent No.: US 11,865,200 B2
(45) Date of Patent: *Jan. 9, 2024

(54) CHEMICAL COMPOSITION AND RELATED METHODS

(71) Applicants: Michael E. Stein, New Philadelphia, OH (US); Sean A. Dickson, Canton, GA (US)

(72) Inventors: Michael E. Stein, New Philadelphia, OH (US); Sean A. Dickson, Canton, GA (US)

( * ) Notice: Subject to any disclaimer, the term of this patent is extended or adjusted under 35 U.S.C. 154(b) by 162 days.

This patent is subject to a terminal disclaimer.

(21) Appl. No.: 17/490,693

(22) Filed: Sep. 30, 2021

(65) Prior Publication Data

US 2022/0105023 A1    Apr. 7, 2022

Related U.S. Application Data

(60) Provisional application No. 63/086,762, filed on Oct. 2, 2020.

(51) Int. Cl.
| | |
|---|---|
| C08K 3/38 | (2006.01) |
| C08L 83/04 | (2006.01) |
| A61K 8/895 | (2006.01) |
| A61Q 17/00 | (2006.01) |
| A61K 8/22 | (2006.01) |

(52) U.S. Cl.
CPC ............... *A61K 8/895* (2013.01); *A61K 8/22* (2013.01); *A61Q 17/005* (2013.01); *C08L 83/04* (2013.01); *C08K 3/38* (2013.01); *C08K 2003/382* (2013.01); *C08K 2003/385* (2013.01); *C08K 2003/387* (2013.01); *C08L 2205/025* (2013.01); *C08L 2205/03* (2013.01)

(58) Field of Classification Search
CPC ..... C08L 83/04; C08K 3/38; C08K 2003/382; C08K 2003/385; C08K 2003/387
USPC .......................................................... 528/24
See application file for complete search history.

(56) References Cited

U.S. PATENT DOCUMENTS

| | | | | |
|---|---|---|---|---|
| 2,442,613 | A * | 6/1948 | Nicodemus | C08K 3/38 |
| | | | | 524/405 |
| 3,070,560 | A * | 12/1962 | Metevia | C08K 5/55 |
| | | | | 528/42 |
| 5,977,220 | A * | 11/1999 | Burkus, II | C08K 5/19 |
| | | | | 528/21 |
| 9,671,085 | B2 | 6/2017 | Brunt, Jr. et al. | |
| 11,505,676 | B2 * | 11/2022 | Chen | C08G 77/20 |
| 2010/0105823 | A1 * | 4/2010 | Georges | H01B 3/46 |
| | | | | 524/398 |

FOREIGN PATENT DOCUMENTS

| | | |
|---|---|---|
| CN | 102893417 B | 1/2013 |
| JP | 5746620 B2 | 12/2012 |
| KR | 20190056597 A | 5/2019 |

* cited by examiner

*Primary Examiner* — Margaret G Moore

(57) ABSTRACT

A composition having: 30% to 35% by weight of a first polydimethylsiloxane having vinyl moieties, wherein at least 0.10% by weight of the first polydimethylsiloxane is attributed to the vinyl moieties; 20% to 25% by weight of a second polydimethylsiloxane having vinyl moieties, wherein at least 0.20% by weight of the second polydimethylsiloxane is attributed to the vinyl moieties; 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide, wherein the fumed silicon dioxide has a surface area of at least 150 square meters per gram; 0.15% to 0.5% by weight active boron; and 0.25% to 1.00% by weight active peroxide.

25 Claims, No Drawings

CHEMICAL COMPOSITION AND RELATED METHODS

CROSS-REFERENCE TO RELATED APPLICATIONS

This patent application claims priority to U.S. provisional patent application Ser. No. 63/086,762 that has a filing date of Oct. 2, 2020. The subject matter of U.S. provisional patent application Ser. No. 63/086,762 is hereby incorporated by reference into this application.

BACKGROUND OF THE INVENTION

There remains a need for anti-microbial, anti-fungal, and anti-viral compositions and related methods. There also remains a need for compositions and related methods directed to manufacturing articles that are viral-resistant, fungal-resistant, microbial-resistant, and combinations thereof.

BRIEF SUMMARY OF THE INVENTION

A composition having: 30% to 35% by weight of a first polydimethylsiloxane having vinyl moieties, wherein at least 0.10% by weight of the first polydimethylsiloxane is attributed to the vinyl moieties; 20% to 25% by weight of a second polydimethylsiloxane having vinyl moieties, wherein at least 0.20% by weight of the second polydimethylsiloxane is attributed to the vinyl moieties; 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide, wherein the fumed silicon dioxide has a surface area of at least 150 square meters per gram; 0.15% to 0.5% by weight active boron; and 0.25% to 1.00% by weight active peroxide.

DETAILED DESCRIPTION OF THE INVENTION

Embodiments are directed to compositions and methods having use in the following types of applications: anti-viral, anti-fungal, anti-microbial, and combinations thereof. In additional embodiments, the compositions and methods are: viral resistant, fungal resistant, microbial resistant, and combinations thereof. In embodiments, an inventive composition is contacted with a substrate. As non-limiting examples, substrate surfaces include: a human-skin surface, an animal-skin surface, and a solid-phase substrate surface of any kind. Compositional embodiments may also be contacted with a liquid-phase composition or a gas-phase composition. A compositional embodiment's duration of contact with a surface or phase-specific composition is a variable that affects the degree of anti-viral, anti-fungal, or anti-microbial effect on the surface. In other embodiments, the inventive compositions are used to manufacture articles.

In a first embodiment, a useful composition includes: 30% to 35% by weight of a first polydimethylsiloxane having vinyl moieties, wherein at least 0.10% by weight of the first polydimethylsiloxane is attributed to the vinyl moieties, 20% to 25% by weight of a second polydimethylsiloxane having vinyl moieties; wherein at least 0.20% by weight of the second polydimethylsiloxane is attributed to the vinyl moieties, 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide; wherein the fumed silicon dioxide has a surface area of at least 150 square meters per gram; 0.2% to 1.0% by weight a blowing agent; 0.15% to 0.5% by weight active boron; and 0.25% to 1.00% by weight active peroxide.

A second embodiment is a directed to a method having the step of crosslinking a composition having: 30% to 35% by weight of a first polydimethylsiloxane having vinyl moieties, wherein at least 0.10% by weight of the first polydimethylsiloxane is attributed to the vinyl moieties, 20% to 25% by weight of a second polydimethylsiloxane having vinyl moieties; wherein at least 0.20% by weight of the second polydimethylsiloxane is attributed to the vinyl moieties, 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide; wherein the fumed silicon dioxide has a surface area of at least 150 square meters per gram; 0.2% to 1.0% by weight a blowing agent; 0.15% to 0.5% by weight active boron; and 0.25% to 1.00% by weight active peroxide.

A third embodiment is directed to a product produced by a process having the step of crosslinking a composition comprising: 30% to 35% by weight of a first polydimethylsiloxane having vinyl moieties, wherein at least 0.10% by weight of the first polydimethylsiloxane is attributed to the vinyl moieties, 20% to 25% by weight of a second polydimethylsiloxane having vinyl moieties; wherein at least 0.20% by weight of the second polydimethylsiloxane is attributed to the vinyl moieties, 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide; wherein the fumed silicon dioxide has a surface area of at least 150 square meters per gram; 0.2% to 1.0% by weight a blowing agent; 0.15% to 0.5% by weight active boron; and 0.25% to 1.00% by weight active peroxide.

A fourth embodiment is directed to a composition having: 30% to 35% by weight of a first polydimethylsiloxane having vinyl moieties, wherein at least 0.10% by weight of the first polydimethylsiloxane is attributed to the vinyl moieties, 20% to 25% by weight of a second polydimethylsiloxane having vinyl moieties; wherein at least 0.20% by weight of the second polydimethylsiloxane is attributed to the vinyl moieties, 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide; wherein the fumed silicon dioxide has a surface area of at least 150 square meters per gram; 0.15% to 0.5% by weight active boron; and 0.25% to 1.00% by weight active peroxide.

A fifth embodiment is directed to a method having the step of crosslinking a composition comprising: 30% to 35% by weight of a first polydimethylsiloxane having vinyl moieties, wherein at least 0.10% by weight of the first polydimethylsiloxane is attributed to the vinyl moieties, 20% to 25% by weight of a second polydimethylsiloxane having vinyl moieties; wherein at least 0.20% by weight of the second polydimethylsiloxane is attributed to the vinyl moieties, 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide; wherein the fumed silicon dioxide has a surface area of at least 150 square meters per gram; 0.15% to 0.5% by weight active boron; and 0.25% to 1.00% by weight active peroxide.

A sixth embodiment is directed to a product produced by a process having the step of crosslinking a composition comprising: 30% to 35% by weight of a first polydimethylsiloxane having vinyl moieties, wherein at least 0.10% by weight of the first polydimethylsiloxane is attributed to the vinyl moieties, 20% to 25% by weight of a second polydimethylsiloxane having vinyl moieties; wherein at least 0.20% by weight of the second polydimethylsiloxane is attributed to the vinyl moieties, 7% to 10% by weight of a third polydimethylsiloxane having hydroxyl moieties, wherein at least 2.0% by weight of the third polydimethylsiloxane is attributed to the hydroxyl moieties; 22% to 35% by weight fumed silicon dioxide; wherein the fumed silicon dioxide has a surface area of at least 150 square meters per gram; 0.15% to 0.5% by weight active boron; and 0.25% to 1.00% by weight active peroxide.

In any of the above first through sixth embodiments, an additional phosphorescent component may be included in an amount ranging from 1-20%. Any composition known to be phosphorescent may be used as the phosphorescent component. Non-limiting examples of useful phosphorescent components include strontium aluminate, europium dysprosium, yttrium oxide, calcium sulfide, or a combination thereof.

In any of the above first through sixth embodiments, an additional reflective component may be included in an amount ranging from 1-20%. Any composition known to be reflective may be used as the reflective component. Non-limiting examples of useful reflective components include mica that is coated with metal oxide, titanium dioxide, tin oxide, iron oxide, organic pigment, synthetic pigment, or a combination thereof.

In any of the above first through sixth embodiments, two additional components may be added. The first component being a phosphorescent component that is added in an amount ranging from 1-10%, and the second component being a reflective component that is added in an amount ranging from 1-10%. Non-limiting examples of useful phosphorescent components include strontium aluminate, europium dysprosium, yttrium oxide, calcium sulfide, or a combination thereof. Non-limiting examples of useful reflective components include mica that is coated with metal oxide, titanium dioxide, tin oxide, iron oxide, organic pigment, synthetic pigment, or a combination thereof.

In any of the above embodiments, zinc oxide, i.e., ZnO, may be added in an amount ranging from 2% to 10% by weight. In these embodiments, the amount of fumed silicon dioxide in the formulation is reduced by the same amount of zinc oxide being added.

Regarding the first polydimethylsiloxane described in the above embodiments, polydimethylsiloxanes having vinyl moieties are well known and commercially available. Still further, polydimethylsiloxanes having vinyl moieties that make up at least 0.10% by weight of the polydimethylsiloxane are well known and commercially available. Persons having ordinary skill in the art will be able to acquire these polydimethylsiloxanes having vinyl moieties and determine useful amounts within the overall compositional embodiment without having to exercise undue experimentation.

Regarding the second polydimethylsiloxane described in the above embodiments, polydimethylsiloxanes having vinyl moieties are well known and commercially available. Still further, polydimethylsiloxanes having vinyl moieties that make up at least 0.20% by weight of the polydimethylsiloxane are well known and commercially available. Persons having ordinary skill in the art will be able to acquire these polydimethylsiloxanes having vinyl moieties and determine useful amounts within the overall compositional embodiment without having to exercise undue experimentation.

Regarding the third polydimethylsiloxane described in the above embodiments, polydimethylsiloxanes having hydroxyl moieties are well known and commercially available. Still further, polydimethylsiloxanes having hydroxyl moieties that make up at least 2.0% by weight of the polydimethylsiloxane are well known and commercially available. Persons having ordinary skill in the art will be able to acquire these polydimethylsiloxanes having hydroxyl moieties and determine useful amounts within the overall composition without having to exercise undue experimentation.

Fumed silicon dioxide is a commercially available substance, and persons of ordinary skill in the art will be able to acquire and determine useful amounts within the above embodiments without having to exercise undue experimentation. In embodiments, useful fumed silicon dioxide has a surface area of at least 150 square meters per gram. In other embodiments, useful fumed silicon dioxide has a surface area of at least 130 square meters per gram. In still other embodiments, useful fumed silicon dioxide has a surface area of at least 170 square meters per gram.

Blowing agents that are useful in general polymer and polydimethylsiloxane applications are well known and commercially available. Any commercially available blowing agent known to be useful in polydimethylsiloxane can be used in the above embodiments, and persons having ordinary skill in the art will be able to select useful blowing agents without having to exercise undue experimentation.

Active boron is a commercially available substance, and persons of ordinary skill in the art will be able to acquire and determine useful amounts within the above embodiments without having to exercise undue experimentation. In some embodiments, active boron can be understood to be boran in one of its forms.

Active peroxide is a commercially available substance, and persons of ordinary skill in the art will be able to acquire and determine useful amounts within the above embodiments without having to exercise undue experimentation. In some embodiments, active peroxide can be understood to be peroxide in one of its forms.

Zinc-oxide particulates are a commercially available substance, and persons of ordinary skill in the art will be able to acquire and determine useful amounts within the above embodiments without having to exercise undue experimentation. Because zinc-oxide particulates are often not spherical in three-dimensional shape due to agglomeration or other causes of non-spherical uniformity, useful zinc-oxide particulates are described herein as having a size that is described with "a greatest characteristic linear dimension." This dimension is used because it describes the general size of a zinc-oxide particulate without reference to its shape; a linear or straight length is used describe what could be considered the distance from one side of the particulate to the other. In embodiments, each of the zinc-oxide particulates has a greatest characteristic linear dimension that is less than one micron. In additional embodiments, each of the zinc-oxide particulates has a greatest characteristic linear dimension ranging from 10 nanometers to 800 nanometers. In still other embodiments, each of the zinc-oxide particulates has a greatest characteristic linear dimension ranging from 100 nanometers to 500 nanometers.

In embodiments, the zinc-oxide particulates are surface modified. Non-limiting examples of substances that can be used to modify a surface of a zinc-oxide particulate include: a silane coating, a silazane coating, a siloxane coating, a cyclic silazane coating, a cyclic siloxane coating, a diol coating, an alcohol coating, a stearate coating, a cyanurate coating, an oxide coating, or combinations thereof.

Compositional embodiments can be compounded using all known polymer compounding processes. Non-limiting examples of useful compounding methods include Banbury compounding, dough mixing, kneader mixing, planetary-mixing, open two-or-three roll mill mixing, twin-screw compounding using known screw configurations and heating-zone barrel configurations, and single-screw compounding using known screw configurations and heating-zone barrel configurations. In embodiments, the compounded compositional embodiments are pelletized or extruded into sheets for further manufacturing of articles.

Crosslinking processes are well known, and any known process for cross-linking any of the compositional embodiments can be used during the compounding or to manufacture and article of manufacture. As a non-limiting example, the compositional embodiments will crosslink via an organic peroxide that is exposed to an external heat source.

In embodiments, a useful specific gravity is at least 0.30 grams per cubic centimeter. In other compositional embodiments, useful specific gravities range from 0.30 grams per cubic centimeter to 1.00 grams per cubic centimeter.

In embodiments, a composition has a compression deflection at 25% deflection ranging from 1 pound per square inch to 25 pounds per square inch.

In embodiments, compositions provide any of the following properties or combinations thereof: anti-viral properties, anti-fungal properties, anti-microbial properties. In embodiments, this can be done by contacting a compositional embodiment, whether crosslinked or not, with a human-skin surface or animal-skin surface.

In embodiments, compositions may be used to prevent humans or animals from acquiring a virus, fungus, or microbes.

Any known polymeric article of manufacture can be manufactured using one or more the embodiments. Non-limiting examples include: a composite wire, a wire coating, or a pipe that directs fluid flow. Additional non-limiting examples include: a wrapping tape, a handle for a sporting-equipment apparatus, a baseball bat, a baseball-bat handle, a tennis racket, a tennis-racket handle, a hockey stick, a hockey-stick handle, a golf club, a golf-club grip, a bicycle, a bicycle handlebar grip, a motorcycle, a motorcycle hand grip, a firearm, a firearm grip, a firearm forend wrap, a hunting-bow handle, a hunting-bow limb-and-string damper, a hunting stand, a fishing net, a fishing-net handle, a fishing pole, a fishing-pole handle, a steering wheel, an automotive steering wheel, a door handle, a mass-transit passenger-compartment railing, a mass-transit passenger-compartment bench, a mass-transit passenger-compartment seat, a chair, a construction hand tool, a hammer, a construction power tool, a forklift steering wheel, an actuation lever, a stair rail, a shopping cart, a shopping-cart handle, a bandage, a hospital bed, a wheelchair, an elastic bandage, a tourniquet, an arm sling, a surgery-equipment handle, a cooking-utensil handle, a beverage-machine handle, commercial water-pipe insulation, commercial fluid-pipe insulation, commercial gas-pipe insulation, commercial fuel-pipe insulation, commercial ventilation-pipe insulation, electrical-conduit insulation, electrical-wire insulation, a mixing tank, a storage tank, a storage vessel, mixing-tank insulation, storage-tank insulation, storage-vessel insulation, surgical equipment, a surgical tray, a lighting apparatus, a hospital gurney, or an operating table.

EXPERIMENTAL

The below two tables of test results respectively titled, "FUSEALL GENERAL PURPOSE" and the immediately following table titled, "Air Aging Properties—From Wrap not ASTM slabs" are for the following formulation:

A composition having:
30% to 35% by weight of a first polydimethylsiloxane having vinyl moieties, wherein at least 0.10% by weight of the first polydimethylsiloxane is attributed to the vinyl moieties;
20% to 25% by weight of a second polydimethylsiloxane having vinyl moieties, wherein at least 0.20% by weight of the second polydimethylsiloxane is attributed to the vinyl moieties;
7% to 10% by weight of a third polydimethylsiloxane having hydroxyl moieties, wherein at least 2.0% by weight of the third polydimethylsiloxane is attributed to the hydroxyl moieties;
22% to 35% by weight fumed silicon dioxide, wherein the fumed silicon dioxide has a surface area of at least 150 square meters per gram;
0.2% to 1.0% by weight a blowing agent;
0.15% to 0.5% by weight active boron; and
0.25% to 1.00% by weight active peroxide.

| FUSEALL ™ GENERAL PURPOSE | | |
|---|---|---|
| Property | Test Method | Typical Value |
| Color | | Any |
| Thickness mm | | 1.5 |
| (inches) | | 0.060" |
| Standard Width, mm | | 25 |
| (inches) | | 1 |
| Duro Hardness, Shore O | D-2240 | 40 |
| Density, g/cc | | 0.55-1.00 |
| Tensile Strength, psi | D-412 | 250 |
| Elongation, % | D-412 | 500 |
| Compression Set 22 hrs. @ 100 C. (21.2 F.) | D-395 | 9% |
| Rebound Resilience Pendulum (J*m−3) | ASTM D7121 | 32.6 |
| Thermal Conductivity 25 C. (77 F.), W/m Deg LK | ASTM E1530 | 0.133 |
| Water Absorption 46 hrs. in H20 @21 C. (69.8 F.) | Mil-I-46852C | 0.08 |
| Thickness FIT-930-101-10' | | 0.06" |
| Dielectric Strength volts/mi | ASTM D149 | 280 |
| Bond Strength Lb-in | Mil-I-46852C | 2.94 |
| Low Temp Brittleness 3 min at −65 C. (−149 F.) | ASTM D2137 A-A-59588 Cl 2A | Pass |

| Air Aging Properties - From Wrap not ASTM slabs | | |
|---|---|---|
| 70 hrs. @ 225 C. (437 F.) ASTM D573 | | |
| Duro Hardness, Shore O | D-2240 | 47 (+7) |
| Tensile Strength | D-412 | 225 |
| Elongation | D-412 | 225 |
| Bend (Flat) | No Cracks | No Cracks |
| 24 hrs. @ 260 C. (500 F.) ASTM D573 | | |
| Duro Hardness, Shore O | D-2240 | 45 (+4) |
| Tensile Strength | D-412 | 222 |
| Elongation | D-412 | 180 |
| Bend (Flat) | No Cracks | No Cracks |

The below table of test results titled, "FUSEALL HIGH TEMPERATURE" and the immediately following table titled, "Air Aging Properties—From Wrap not ASTM slabs" are for the following formulation:

A composition having:
- 30% to 35% by weight of a first polydimethylsiloxane having vinyl moieties, wherein at least 0.10% by weight of the first polydimethylsiloxane is attributed to the vinyl moieties;
- 20% to 25% by weight of a second polydimethylsiloxane having vinyl moieties, wherein at least 0.20% by weight of the second polydimethylsiloxane is attributed to the vinyl moieties;
- 7% to 10% by weight of a third polydimethylsiloxane having hydroxyl moieties, wherein at least 2.0% by weight of the third polydimethylsiloxane is attributed to the hydroxyl moieties;
- 22% to 35% by weight fumed silicon dioxide, wherein the fumed silicon dioxide has a surface area of at least 150 square meters per gram;
- 0.2% to 1.0% by weight a blowing agent;
- 0.15% to 0.5% by weight active boron;
- 0.25% to 1.00% by weight active peroxide; and
- 1% to 2% by weight a heat stabilizer selected from the group consisting of barium zirconate, rare earth octoate, manganese octoate, fumed titanium dioxide, cerium hydrate, cerium oxide, manganese oxide, ferric oxide, and combinations thereof.

| FUSEALL ™ HIGH TEMPERAUTURE | | |
|---|---|---|
| Property | Test Method | Typical Value |
| Color | | Any |
| Thickness mm | | 1.5 |
| (inches) | | 0.060" |
| Standard Width, mm | | 25 |
| (inches) | | 1 |
| Duro Hardness, Shore O | D-2240 | 41 |
| Density, g/cc | | 0.55-1.00 |
| Tensile Strength, psi | D-412 | 210 |
| Elongation, % | D-412 | 19 |
| Compression Set 22 hrs. @ 100 C. (21.2 F.) | D-395 | 8% |
| Rebound Resilience Pendulum (J*m−3) | ASTM D7121 | 30.8 |
| Thermal Conductivity 25 C. (77 F.), W/m Deg LK | ASTM E1530 | 0.158 |
| Water Absorption 46 hrs. in H20 @21 C. (69.8 F.) | Mil-I-46852C | 0.08 |
| Thickness FIT-930-101-10' | | 0.06" |
| Dielectric Strength volts/mi | ASTM D149 | 280 |
| Bond Strength Lb-in | Mil-I-46852C | 226 |
| Low Temp Brittleness 3 min at −65 C. (−149 F.) | ASTM D2137 A-A-59588 Cl 2A | Pass |

| Air Aging Properties - From Wrap not ASTM slabs | | |
|---|---|---|
| 70 hrs. @ 225 C. (437 F.) ASTM D573 | | |
| Duro Hardness, Shore O | D-2240 | 47 (+6) |
| Tensile Strength | D-412 | 242 |
| Elongation | D-412 | 186 |
| Bend (Flat) | No Cracks | No Cracks |
| 24 hrs. @ 260 C. (500 F.) ASTM D573 | | |
| Duro Hardness, Shore O | D-2240 | 44 (+3) |
| Tensile Strength | D-412 | 231 |
| Elongation | D-412 | 177 |
| Bend (Flat) | No Cracks | No Cracks |

What is claimed is:

1. A composition comprising:
   - 30% to 35% by weight of a first polydimethylsiloxane having vinyl moieties,
     wherein at least 0.10% by weight of the first polydimethylsiloxane is attributed to the vinyl moieties;
   - 20% to 25% by weight of a second polydimethylsiloxane having vinyl moieties,
     wherein at least 0.20% by weight of the second polydimethylsiloxane is attributed to the vinyl moieties;
   - 7% to 10% by weight of a third polydimethylsiloxane having hydroxyl moieties,
     wherein at least 2.0% by weight of the third polydimethylsiloxane is attributed to the hydroxyl moieties;
   - 22% to 35% by weight fumed silicon dioxide,
     wherein the fumed silicon dioxide has a surface area of at least 150 square meters per gram;
   - 0.15% to 0.5% by weight active boron; and
   - 0.25% to 1.00% by weight active peroxide.

2. The composition of claim 1 further comprising 1-20% by weight phosphorescent component, wherein the phosphorescent component is strontium aluminate, europium dysprosium, yttrium oxide, calcium sulfide, or a combination thereof.

3. The composition of claim 1 further comprising 1-20% by weight reflective component, wherein the reflective component is mica that is coated with metal oxide, titanium dioxide, tin oxide, iron oxide, organic pigment, synthetic pigment, or a combination thereof.

4. The composition of claim 1 further comprising 1-10% by weight phosphorescent component and 1-10% by weight reflective component,
   wherein the phosphorescent component is strontium aluminate, europium dysprosium, yttrium oxide, calcium sulfide, or a combination thereof, and
   wherein the reflective component is mica that is coated with metal oxide, titanium dioxide, tin oxide, iron oxide, organic pigment, synthetic pigment, or a combination thereof.

5. The composition of claim 1, further comprising 1% to 2% by weight a heat stabilizer selected from the group consisting of barium zirconate, rare earth octoate, manganese octoate, fumed titanium dioxide, cerium hydrate, cerium oxide, manganese oxide, ferric oxide, and combinations thereof.

6. The composition of claim 1 further comprising 2.0% to 10% by weight zinc-oxide particulates.

7. The composition of claim 6, wherein each of the zinc-oxide particulates has a greatest characteristic linear dimension that is less than one micron.

8. The composition of claim 6, wherein each of the zinc-oxide particulates has a greatest characteristic linear dimension ranging from 10 nanometers to 800 nanometers.

9. The composition of claim 6, wherein each of the zinc-oxide particulates has a greatest characteristic linear dimension ranging from 100 nanometers to 500 nanometers.

10. The composition of claim 6, wherein the zinc-oxide particulates are surface modified.

11. The composition of claim 10, wherein the zinc-oxide particulates are surface modified with a coating selected from the group consisting of: a silane coating, a silazane coating, a siloxane coating, a cyclic silazane coating, a cyclic siloxane coating, a diol coating, an alcohol coating, a stearate coating, a cyanurate coating, an oxide coating, and combinations thereof.

12. A product produced by the process of crosslinking the composition of claim 1.

13. A product produced by the process of crosslinking the composition of claim 2.

14. A product produced by the process of crosslinking the composition of claim 3.

15. A product produced by the process of crosslinking the composition of claim 4.

16. A product produced by the process of crosslinking the composition of claim 5.

17. A product produced by the process of crosslinking the composition of claim 6.

18. A method comprising the step:
contacting the composition of claim 12 with a human-skin surface or an animal-skin surface.

19. A method comprising the step:
contacting the composition of claim 13 with a human-skin surface or an animal-skin surface.

20. A method comprising the step:
contacting the composition of claim 14 with a human-skin surface or an animal-skin surface.

21. A method comprising the step:
contacting the composition of claim 15 with a human-skin surface or an animal-skin surface.

22. An article of manufacture that includes the product of claim 12, wherein the article of manufacture is: a composite wire, a wire coating, a pipe, a wrapping tape, a handle for a sporting-equipment apparatus, a baseball bat, a baseball-bat handle, a tennis racket, a tennis-racket handle, a hockey stick, a hockey-stick handle, a golf club, a golf-club grip, a bicycle, a bicycle handlebar grip, a motorcycle, a motorcycle hand grip, a firearm, a firearm grip, a firearm forend wrap, a hunting-bow handle, a hunting-bow limb-and-string damper, a hunting stand, a fishing net, a fishing-net handle, a fishing pole, a fishing-pole handle, a steering wheel, an automotive steering wheel, a door handle, a mass-transit passenger-compartment railing, a mass-transit passenger-compartment bench, a mass-transit passenger-compartment seat, a chair, a construction hand tool, a hammer, a construction power tool, a forklift steering wheel, an actuation lever, a stair rail, a shopping cart, a shopping-cart handle, a bandage, a hospital bed, a wheelchair, an elastic bandage, a tourniquet, an arm sling, a surgery-equipment handle, a cooking-utensil handle, a beverage-machine handle, commercial water-pipe insulation, commercial fluid-pipe insulation, commercial gas-pipe insulation, commercial fuel-pipe insulation, commercial ventilation-pipe insulation, electrical-conduit insulation, electrical-wire insulation, a mixing tank, a storage tank, a storage vessel, mixing-tank insulation, storage-tank insulation, storage-vessel insulation, surgical equipment, a surgical tray, a lighting apparatus, a hospital gurney, or an operating table.

23. An article of manufacture that includes the product of claim 13, wherein the article of manufacture is: a composite wire, a wire coating, a pipe, a wrapping tape, a handle for a sporting-equipment apparatus, a baseball bat, a baseball-bat handle, a tennis racket, a tennis-racket handle, a hockey stick, a hockey-stick handle, a golf club, a golf-club grip, a bicycle, a bicycle handlebar grip, a motorcycle, a motorcycle hand grip, a firearm, a firearm grip, a firearm forend wrap, a hunting-bow handle, a hunting-bow limb-and-string damper, a hunting stand, a fishing net, a fishing-net handle, a fishing pole, a fishing-pole handle, a steering wheel, an automotive steering wheel, a door handle, a mass-transit passenger-compartment railing, a mass-transit passenger-compartment bench, a mass-transit passenger-compartment seat, a chair, a construction hand tool, a hammer, a construction power tool, a forklift steering wheel, an actuation lever, a stair rail, a shopping cart, a shopping-cart handle, a bandage, a hospital bed, a wheelchair, an elastic bandage, a tourniquet, an arm sling, a surgery-equipment handle, a cooking-utensil handle, a beverage-machine handle, commercial water-pipe insulation, commercial fluid-pipe insulation, commercial gas-pipe insulation, commercial fuel-pipe insulation, commercial ventilation-pipe insulation, electrical-conduit insulation, electrical-wire insulation, a mixing tank, a storage tank, a storage vessel, mixing-tank insulation, storage-tank insulation, storage-vessel insulation, surgical equipment, a surgical tray, a lighting apparatus, a hospital gurney, or an operating table.

24. An article of manufacture that includes the product of claim 14, wherein the article of manufacture is: a composite wire, a wire coating, a pipe, a wrapping tape, a handle for a sporting-equipment apparatus, a baseball bat, a baseball-bat handle, a tennis racket, a tennis-racket handle, a hockey stick, a hockey-stick handle, a golf club, a golf-club grip, a bicycle, a bicycle handlebar grip, a motorcycle, a motorcycle hand grip, a firearm, a firearm grip, a firearm forend wrap, a hunting-bow handle, a hunting-bow limb-and-string damper, a hunting stand, a fishing net, a fishing-net handle, a fishing pole, a fishing-pole handle, a steering wheel, an automotive steering wheel, a door handle, a mass-transit passenger-compartment railing, a mass-transit passenger-compartment bench, a mass-transit passenger-compartment seat, a chair, a construction hand tool, a hammer, a construction power tool, a forklift steering wheel, an actuation lever, a stair rail, a shopping cart, a shopping-cart handle, a bandage, a hospital bed, a wheelchair, an elastic bandage, a tourniquet, an arm sling, a surgery-equipment handle, a cooking-utensil handle, a beverage-machine handle, commercial water-pipe insulation, commercial fluid-pipe insulation, commercial gas-pipe insulation, commercial fuel-pipe insulation, commercial ventilation-pipe insulation, electrical-conduit insulation, electrical-wire insulation, a mixing tank, a storage tank, a storage vessel, mixing-tank insulation, storage-tank insulation, storage-vessel insulation, surgical equipment, a surgical tray, a lighting apparatus, a hospital gurney, or an operating table.

25. An article of manufacture that includes the product of claim 15, wherein the article of manufacture is: a composite wire, a wire coating, a pipe, a wrapping tape, a handle for a sporting-equipment apparatus, a baseball bat, a baseball-bat handle, a tennis racket, a tennis-racket handle, a hockey stick, a hockey-stick handle, a golf club, a golf-club grip, a bicycle, a bicycle handlebar grip, a motorcycle, a motorcycle hand grip, a firearm, a firearm grip, a firearm forend wrap, a hunting-bow handle, a hunting-bow limb-and-string damper, a hunting stand, a fishing net, a fishing-net handle, a fishing pole, a fishing-pole handle, a steering wheel, an automotive steering wheel, a door handle, a mass-transit passenger-compartment railing, a mass-transit passenger-compartment bench, a mass-transit passenger-compartment seat, a chair, a construction hand tool, a hammer, a construction power tool, a forklift steering wheel, an actuation lever, a stair rail, a shopping cart, a shopping-cart handle, a bandage, a hospital bed, a wheelchair, an elastic bandage, a tourniquet, an arm sling, a surgery-equipment handle, a cooking-utensil handle, a beverage-machine handle, commercial water-pipe insulation, commercial fluid-pipe insulation, commercial gas-pipe insulation, commercial fuel-pipe insulation, commercial ventilation-pipe insulation, electrical-conduit insulation, electrical-wire insulation, a mixing tank, a storage tank, a storage vessel, mixing-tank insulation, storage-tank insulation, storage-vessel insulation, surgical equipment, a surgical tray, a lighting apparatus, a hospital gurney, or an operating table.

\* \* \* \* \*